United States Patent
Litvinov et al.

(10) Patent No.: US 11,821,818 B2
(45) Date of Patent: Nov. 21, 2023

(54) BIOSENSOR FOR DETECTING A SINGLE MAGNETIC LABEL

(71) Applicant: University of Houston System, Houston, TX (US)

(72) Inventors: Dmitri Litvinov, Friendswood, TX (US); Long Chang, Pearland, TX (US); Richard Willson, Houston, TX (US)

(73) Assignee: University of Houston System, Houston, TX (US)

( * ) Notice: Subject to any disclaimer, the term of this patent is extended or adjusted under 35 U.S.C. 154(b) by 476 days.

(21) Appl. No.: 16/624,643

(22) PCT Filed: Jul. 6, 2018

(86) PCT No.: PCT/US2018/041003
§ 371 (c)(1),
(2) Date: Dec. 19, 2019

(87) PCT Pub. No.: WO2019/010361
PCT Pub. Date: Jan. 10, 2019

(65) Prior Publication Data
US 2020/0124569 A1     Apr. 23, 2020

Related U.S. Application Data

(60) Provisional application No. 62/529,052, filed on Jul. 6, 2017.

(51) Int. Cl.
*G01N 27/74*     (2006.01)
*G01N 33/543*    (2006.01)

(52) U.S. Cl.
CPC ..... *G01N 27/745* (2013.01); *G01N 33/54326* (2013.01); *G01N 33/54346* (2013.01); *G01N 33/54373* (2013.01)

(58) Field of Classification Search
CPC ........... G01N 27/745; G01N 33/54326; G01N 33/54346; G01N 33/54373
See application file for complete search history.

(56) References Cited

U.S. PATENT DOCUMENTS 6,201,673 B1    3/2001    Rottmayer et al.
7,284,316 B1    10/2007   Huai et al.
(Continued)

OTHER PUBLICATIONS

Tamanaha CR, Mulvaney SP, Rife JC, Whitman LJ. Magnetic labeling, detection, and system integration. Biosens Bioelectron. Sep. 15, 2008;24(1):1-13. (Year: 2008).*
(Continued)

*Primary Examiner* — Rebecca M Giere
(74) *Attorney, Agent, or Firm* — Shackelford, Bowen, McKinley & Norton, LLP (57) ABSTRACT

A biosensor may provide a magnetoresistive (MR) film comprising a nonmagnetic layer may be sandwiched between the two ferromagnetic layers. The MR film may be positioned on a substrate, where the edges of the MR film are in contact with leads. Additionally, the leads may be in contact with pads. The sensors may provide quasi-digital readout that enable greatly enhanced sensitivity. In some embodiments, biosensors may be arranged as array of sensors. The array of sensors may be arranged as a symmetric or asymmetric $N_1 \times N_2$ array, where $N_1$ and $N_2$ are integers, $N_1$ represents the number of sensors linked together in series, and $N_2$ represents the number of sensor sets in parallel, where each sensor set may comprise one or more sensors. Further, the array of sensors may be coupled to a voltmeter, which may be a single voltmeter in some cases that allows the sensors to all be probed simultaneously.

7 Claims, 7 Drawing Sheets

(56) References Cited

U.S. PATENT DOCUMENTS

| | | | |
|---|---|---|---|
| 8,456,157 B2 | 6/2013 | Litvinov et al. | |
| 2004/0023365 A1* | 2/2004 | Engel | B82Y 15/00 |
| | | | 435/287.2 |
| 2004/0120185 A1 | 6/2004 | Kang et al. | |
| 2013/0321954 A1 | 12/2013 | Tsoukatos et al. | |
| 2014/0005517 A1 | 1/2014 | Nagarkar et al. | |

OTHER PUBLICATIONS

Rife et al. (Design and performance of GMR sensors for the detection of magnetic microbeads in biosensors, Sensors and Actuators A: Physical, vol. 107, Issue 3, 2003, pp. 209-218, ISSN 0924-4247, https://doi.org/10.1016/S0924-4247(03)00380-7 (Year: 2003).*

Qiu, Wenlan, et al., "GMR-Based Single-Domain Magnetic Sensor for 500nm Single Particle Detection", University of Houston Intermag Poster, 2017.

Liang, Yu-Chi, et al., "Ultrasensitive Magnetic Nanoparticle Detector for Biosensor Applications", Sensors 2017, 17, 1296; doi:10.3390/s17061296.

Qiu, Wenlan, et al., "Spin-Valve based magnetoresistive nanoparticle detector for applications in biosensing", Sensors and Actuators A 265 (2017) 174-180.

Baselt et al., A biosensor based on magnetoresistance technology, Biosensors & Bioelectronics 13 (1998) 731-739.

\* cited by examiner

BIOSENSOR FOR DETECTING A SINGLE MAGNETIC LABEL

RELATED APPLICATIONS

This application claims the benefit of U.S. Provisional Patent Application No. 62/529,052 filed on Jul. 6, 2017, which is incorporated herein by reference.

STATEMENT REGARDING FEDERALLY SPONSORED RESEARCH

This invention was made with government support under CBET-0932971, awarded by the National Science Foundation, and 1RC1RR028465, awarded by the National Institutes of Health. The government has certains rights in the invention.

FIELD OF THE INVENTION

This invention relates to a biosensor system, corresponding method for fabrication, and corresponding methods for testing. More particularly, to a biosensor capable of detecting a single magnetic label.

BACKGROUND OF INVENTION

Existing convenient technologies are not capable of detecting the presence of a single molecule. Large (many microns) magnetoresistive (MR) sensors require a large number of reporters to produce a detectable signal and need meticulous calibration that is not practical in the clinic, field or home. Small MR sensors are sensitive to a single reporter, but the probability of a molecule or reporter landing on a single tiny sensor is approximately zero. This disclosure describes a method to link small sensors together in large numbers, and a quasi-digital detection scheme that enables competitive or better sensitivity using less expensive and more robust readout electronics.

Binding assays are biochemical tests used in the medical community for diagnostic or research purposes. The test measures the presence or concentration of a molecule called an analyte by labeling/tagging the molecule with a reporter that can be physically measured. Many assays use fluorescent labels which do not have the sensitivity to detect the presence of a single analyte or extremely dilute concentrations. Single molecule detection is hindered due to issues such as sample turbidity, autofluorescence and photobleaching which increases the complexity of the diagnostic system and reduces the signal to noise ratio (SNR).

Magnetoresistive (MR) sensors was introduced by Baselt in 1998 as a possible alternative to fluorescent and enzymatic biomarker assays. MR sensors are compact, inexpensive to manufacture, and highly sensitive. However, state-of-the-art MR based platforms for diagnostic requires hundreds to thousands of magnetic nanoparticles (MNPs) in order to detect concentrations in the low femtomoles, which is approximately 100 times better than leading commercial fluorescent based platforms. Prior sensors are discussed in U.S. Pat. No. 8,456,157, which is incorporated herein by reference.

The change in resistance of an MR sensor is proportional to the coverage of MNPs on the sensor's surface. In order to make precise resistance measurements, which maximizes the sensitivity of the sensor, a Wheatstone bridge is often used. A full bridge is typically constructed using two MR sensors and two tuning resistors. One MR sensor is biologically active and the other is a reference sensor that is located near the active sensor such that it experiences the same sensing environment, such as magnetic fields and temperature. The bridge is balanced by adjusting the tuning resistors. The differential output of a balanced bridge cancels the common mode signal experienced by both the active and reference sensor. If the bridge is not balanced or loses balance due to thermal drift or aging effects, interpretation of the signal is compromised, thereby limiting the practical sensitivity of the device. For example, the temperature coefficient of GMR sensors are approximately 1000 PPM/° C. and trim pots are approximately 100 PPM/° C., so a 1 degree difference in ambient temperature results in a change in resistance that is 90 times larger than a 10 PPM change in resistance detectable in research instruments.

High sensitivity can be achieved in a different manner by shrinking the size of the MR sensor to approximately the size of a MNP. In contrast to large MR sensors, which dedicate the resistance change bandwidth to count MNPs, small MR sensors dedicate the entire bandwidth to detect a single MNP. Quasi-digital MR sensors discussed further herein can enable reliable single molecule detection using less precise measurement techniques.

SUMMARY OF INVENTION

In one embodiment, a biosensor may provide a magnetoresistive (MR) film comprising a buffer or seed layer, magnetic layers, a nonmagnetic layer, and a cap. The magnetic layers may be ferromagnetic, antiferromagnetic, synthetic antiferromagnetic or a combination thereof. The nonmagnetic layer may be sandwiched between the two magnetic layers. The MR film may be positioned on a substrate, where the edges of the MR film are in contact with leads. Additionally, the leads may be in contact with pads. The sensors may provide quasi-digital readout that enable greatly enhanced sensitivity. In some embodiments, biosensors may be arranged as an array of sensors. The array of sensors may be arranged as a symmetric or asymmetric $N_1 \times N_2$ array, where $N_1$ and $N_2$ are integers, $N_1$ represents the number of sensors linked together in series, and $N_2$ represents the number of sensor sets in parallel, where each sensor set may comprise one or more sensors. Further, the array of sensors may be coupled to a voltmeter or the like, which may be a single voltmeter in some cases that allows the sensors to be probed simultaneously.

In yet another embodiment, the steps of forming a biosensor may include depositing a MR film, which may be a multi-layered film as discussed previously, at a desired location. A bilayer resist may be deposited on the MR film, and subsequently patterned into a long line pattern or T-shaped resist structure. The pattern may be transferred to the MR film, and then leads may be deposited. Next, the remaining bilayer resist may be removed, and a $2^{nd}$ bilayer resist may be deposited and patterned into a long line pattern or T-shaped resist structure. Notably, the $2^{nd}$ bilayer resist may be patterned orthogonally to the prior pattern/structure of the initial bilayer resist. Subsequently, the pattern of the $2^{nd}$ bilayer resist may be transferred to the MR and lead films, and the remaining $2^{nd}$ bilayer resist may be removed. After removal of the resist, pads may be deposited on the leads. Sensor chips formed in such embodiments above may be bonded to a printed circuit board (PCB) with an anisotropic conducting film (ACF).

In yet another embodiment, sensors of the various embodiments may be utilized for biochemical testing. The surface of MR sensor may be functionalized with a first analyte binding agent. A magnetic field sweep may be applied to the sensor, and the resistance of the sensor may be monitored for changes in the resistance state. Next, an analyte that is capable of interacting with the first analyte binding agent is introduced to the sensor. Subsequently, magnetic nanoparticles (MNPs) functionalized with a second analyte binding agent may be introduced. Application of a magnetic field sweep and resistance monitoring may be repeated. Notably, a shift in a switching field indicates the presence of at least one of the MNPs on the MR sensors array.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

A system and method for detecting the presence or absence of a target molecule(s) in a binding assay with potentially single molecule sensitivity are discussed herein. The quasi-digital magnetic field sensor(s) or arrays thereof switches between distinctive states in response to a change in the local magnetic field due to the presence of a nearby magnetic nanoparticle reporter. The signal produced by a single magnetic reporter is so strong that it can be detected with a digital voltmeter, multimeter, or any device suitable for measuring resistance. The detection of a reporter in a binding assay thereby corresponds to the presence of a target molecule.

Methodology

Figures 1A, 1B, 1C, 1D:
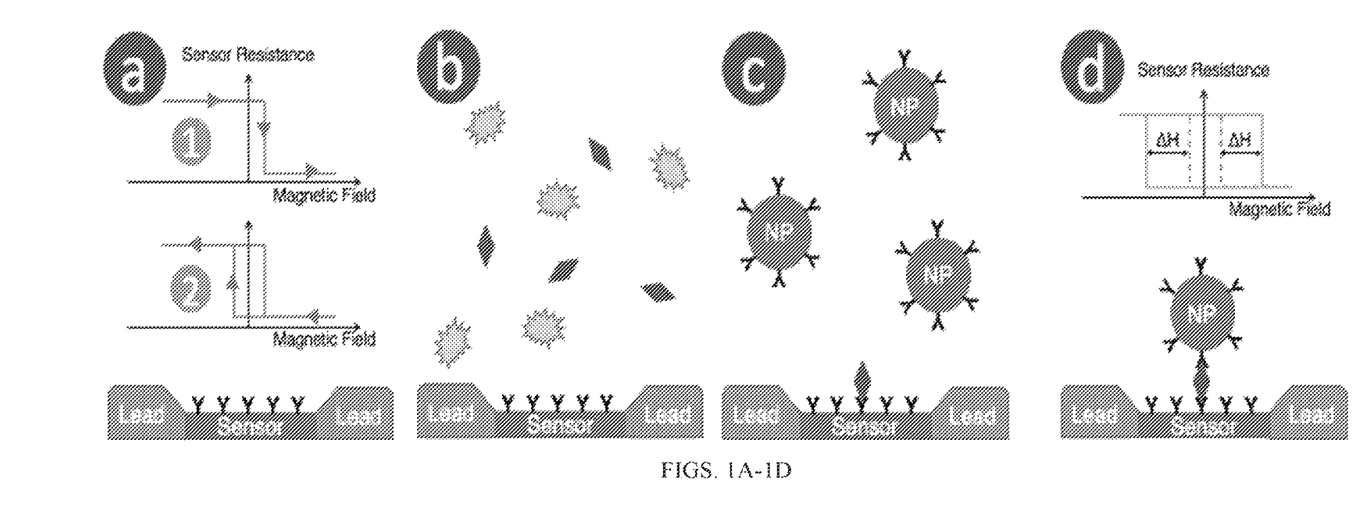
FIGS. 1A-1D show an illustrative embodiment of a binding assay using a quasi-digital MR sensor.

A binding assay using a quasi-digital MR sensor is illustrated in FIGS. 1A-1D. In FIG. 1A, the sensor surface is functionalized with a first analyte binding agent, such as capture antibodies or the like. The arrangement of the MR sensor corresponds to any of the discussed in further detail below. The MR sensor's switching response (R-H curve) is recorded by applying a low frequency AC magnetic field and measuring the resistance. As the magnetic field is swept through a desired range, such as from −400 Oe to 400 Oe, the sensor switches resistance states, such as from a high resistance state to a low resistance state or vice versa (see top plot in FIG. 1A), and the sensor is monitored for such transition point(s) where the resistance state switches. In some embodiments, the magnetic field may be swept forward, backwards, or both. As the transitions between resistance states are discrete, the improved MR sensor's operation may be characterized as a "digital" or "quasi-digital" mode. In contrast, prior art sensors do not involve such discrete resistance states, and as such, operate in an "analog" mode. When the magnetic field is swept in the opposite direction, such as from 400 Oe to −400 Oe, the sensor switches from the low resistance state to a high resistance state (see bottom plot in FIG. 1A). As shown, the transition points where the resistance states switch may be different for the forward sweep and backward sweep. In contrast to prior sensors that detect changes in resistance, the improved sensors discussed herein detect a shift in the switching field where the sensor transition between resistance states. Further, prior sensors often require signal processing or SNR enhancement due to poor signal strength, whereas the improved sensor does not require signal processing, SNR enhancement or the like due to the strength of the signal. Then, the analyte, which may include targeted antigens in some embodiments, are introduced and interacts with the first analyte binding agent or capture antibodies, as shown in FIG. 1B. Biomolecules in the analyte that do not bind to the capture antibodies are washed away. Then, magnetic nanoparticles (MNPs or NPs) functionalized with a second analyte binding agent, such as target antibodies or the like, are introduced and interact with any captured antigens, as shown in FIG. 1C. The first and second analyte binding agents capable of interacting or bonding with the analyte, and the analyte binding agents may be the different or the same. MNPs that are not bound to the sensor via the analyte are washed away. Then, the magnetic field sweep may be performed again as discussed above, and the sensor's switching response is recorded again. It shall be apparent that switching fields for the same direction should be compared since they vary depending on the direction of the sweep. For example, forward switching fields before and after introduction of the analyte and MNPs are compared, backward switching fields before and after introduction of the analyte and MNPs are compared, or both. When a MNP is present on the sensor, the fringe field generated by the MNP reduces the effective field experienced by the sensor. This results in a noticeable shift ($\Delta H$) in the switching field of the sensor as illustrated in FIG. 1D.

One of the novelties of the disclosed quasi-digital MR sensor lies in the detection method where a change in the switching field determines the presence of an MNP. Unlike analog MR sensors which are designed to switch gradually and continuously between its low and high resistance state, the quasi-digital MR sensor is designed to switch discretely between its low and high resistance state. This quasi-digital detection method eliminates the need for precision resistance measurements. For example, the state-of-the-art analog MR sensors need to be capable of detecting a very small, 1 PPM, change in resistance to determine the presence of one MNP, while the quasi-digital MR sensor merely needs to detect a noticeable change in resistance to determine the presence of a single MNP. Another important difference is that conventional MR sensors correlate the change in resistance to an amount of MNPs on the sensor, but it is difficult to determine whether the change in resistance is caused by Wheatstone bridge imbalance due to temperature, temperature gradients, stress, aging, or other effects that changes the resistance of bridge components. In contrast, the quasi-digital MR sensor is directly detecting a change in the local magnetic field or the transition point(s) that correspond to switching between the resistive states. A Wheatstone bridge circuit is not necessary for the quasi-digital MR sensor to detect the presence of a single MNP. It is also not necessary to employ narrow band detection schemes to improve the signal to noise ratio (SNR). Further, the quasi-digital MR sensor may be measured directly using a DC voltmeter or the like, such as a Keithley 2400.

Examples discussed herein are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

MR Sensor

A MR film of a biosensor may provide a spin-valve sandwich structure, which includes two magnetic layers separated by a nonmagnetic spacer. Further, the MR film may optionally form a structure of B/FM/NM/FM/C, in which B designates a buffer/seed layer which promotes desirable growth and material properties of successive layers, C designates a cap layer which protects the MR film from damage, FM designates a ferromagnetic layer (e.g. Fe, Co, Ni), their alloys and multilayers, and/or alloys of the above with nonmagnetic additives (e.g. B, Ta, Ru, Cr, Pt), and NM designates a non-ferromagnetic layer (transition metal, e.g. Cu) and/or noble metal (e.g. Au, or ultrathin insulator layer, e.g. aluminum oxide or magnesium oxide). The overall resistance of such MR film depends on the mutual alignment of the magnetization of the two ferromagnetic layers. When the magnetic layers have parallel magnetization directions, the structure is in its low-resistance state. Antiparallel orientation of the magnetic layers leads to a high-resistance state. The ratio of the resistance change between high and low resistance states to the low resistance state is a figure of merit of MR sensors because higher MR ratios enable higher signal-to-noise ratios and higher dynamic range. The magnetization of one magnetic layer or pinned layer is engineered to be pinned by exchange interaction to a synthetic antiferromagnetic layer, while the other layer or free layer is designed to rotate its magnetization orientation freely.

Figure 2:
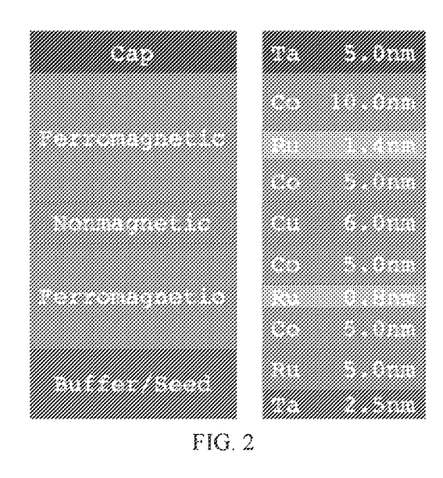
FIG. 2 shows an illustrative embodiment of a MR film or a spin-valve GMR structure.

In some embodiments, a biosensor system may comprise one or more MR sensors providing a quasi-digital response for detecting an analyte that has a spin-valve sandwich structure comprising a nonmagnetic layer sandwiched between two magnetic or ferromagnetic layers. The MR sensors may optionally include cap and/or buffer/seed layers to improve performance, aid manufacturing, or the like. The quasi-digital response may be influence by sensor design features, such as (a) sensor size that is smaller than the magnetic domain, (b) a shape designed to provide some anisotropy to help sensor switch as a single domain, and/or (c) selected materials so that free layer switches at low field and pinned layer does not switch. As a nonlimiting example, the MR sensor may comprise a spin-valve GMR structure or (Ta 2.5 nm/Ru 5 nm/Co 5 nm/Ru 0.8 nm/Co 5 nm/Cu 6 nm/Co 5 nm/Ru 1.4 nm/Co 10 nm/Ta 5 nm) shown in FIG. 2. Embodiments of the MR sensor have a pinned layer (e.g. lower magnetic layer in FIG. 2) and a free layer (e.g. upper magnetic layer in FIG. 2). However, in other embodiments, the position of the free layer may be either on top or on the bottom. Notably, positioning the free layer on the top puts it closer to an MNP, which can increase sensitivity. In some embodiments, the pinned layer comprises at least one layer of magnetic materials and a synthetic antiferromagnetic (SAF) layer, e.g. Co/Ru/Co or the like, to pin magnetization of the magnetic layer by exchange interaction to the SAF layer. In some embodiments, the SAF layer can be replaced with an antiferromagnetic layer (AFM), e.g., IrMn, FeMn, or the like. In some embodiments, the free layer comprises at least one layer of magnetic materials, and can rotate its magnetization orientation freely. The quasi-digital response is caused by the free layer flipping coherently between two states.

It shall be understood that the various layers of the MR sensors may provide one or more layers of materials. In some embodiments, the free layer is designed to switch coherently or instantaneously. A single domain free layer can be achieved using various techniques, such as, but not limited to, small sensor size, shape anisotropy, exchange coupling, selection of particular free layer materials, crystal anisotropy, or the like. In some embodiments, the pinned layer may be designed to switch gradually or instantaneously. If the pinned layer is designed to switch instantaneously, it should have a larger switching field or coercivity than the free layer. Each of the free layer and pinned layer may be composed of any variety of magnetic materials, such as, but not limited to, layers containing ferromagnetic elements (e.g. Ni, Co, Fe, or the like); their alloys (e.g. NiFe, CoFe, or the like); multilayers of ferromagnetic elements and their alloys; and/or alloys of the prior materials listed with non-ferromagnetic elements (e.g. Ru, Ir, Mn, Mg, B, Ta, or the like). In some embodiments, the free layer, pinned layer, or both layers of material may comprise of a synthetic aniferromagnet (SAF). In some embodiments, the free layer may be an asymmetric SAF. In some embodiments, the pinned layer may be a symmetric SAF or ferromagnetic layer with its magnetization pinned by an adjacent antiferromagnetic layer. The switching field distribution of MR sensors may be influence by the shape, materials used, or the like. The free layer may be designed with a low, narrow switching field position to facilitate easy observance of a change in the switching field position when a magnetic reporter is on a sensor. In some embodiments, the shape of the MR sensor may be a shape designed to provide anisotropy to help the sensor switch as a single domain, such as a square, rectangular, oval, square, hexagon, or the like. In some embodiments, the free layer of the sensor may be a polycrystalline or amorphous ferromagnetic layer film, e.g. CoFeB. Without being bound by theory, it is believed that an amorphous layer may be beneficial to a narrow switching field distribution in some embodiments, as the magnetic properties of crystalline materials can sometimes be randomly damaged during fabrication. The composition of the above noted layers may be a single material, a composite, a multilayer or any combination thereof. As a non-limiting example, the pinned layer may be a synthetic antiferromagnet comprising Co/Ru/Co, and the layers may optionally have respective thicknesses 5 nm/0.8 nm/5 nm. As a non-limiting example, the free layer may be an asymmetric synthetic antiferromagnet comprising Co/Ru/Co, and the layers may optionally have respective thicknesses of 5 nm/1.4 nm/10 nm). As another non-limiting example, the free layer may comprise of exchange coupled ferromagnets Co/Ni$_{80}$Fe$_{20}$, and the layers may optionally have thicknesses of 3 nm/10 nm. As a nonlimiting example, the buffer/seed layer may comprise Ta/Ru, and the layers may optionally have respective thicknesses of 5 nm/2.5 nm. As a nonlimiting example, the cap layer may comprise Ta, and the layer may optionally have a thickness of 5 nm.

Figure 3A:
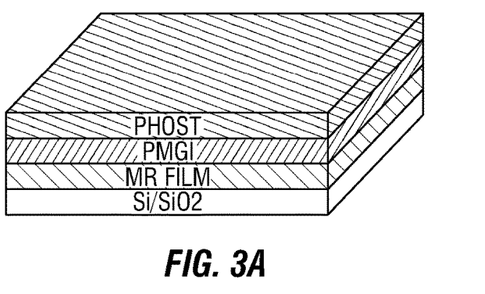
FIGS. 3A-3F illustrate fabrication steps for a biosensor.
Figure 3B:
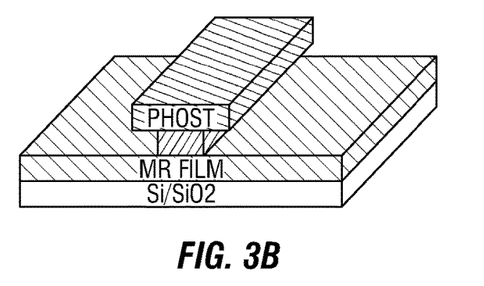
Figure 3C:
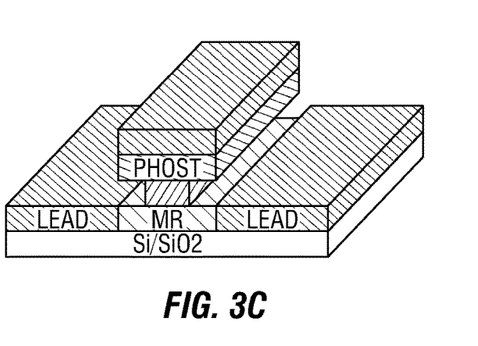
Figure 3D:
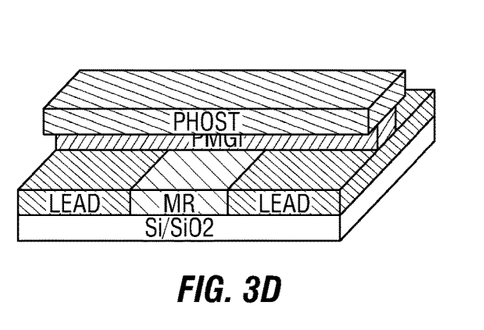
Figure 3E:
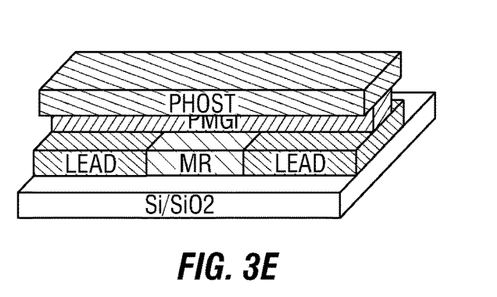
Figure 3F:
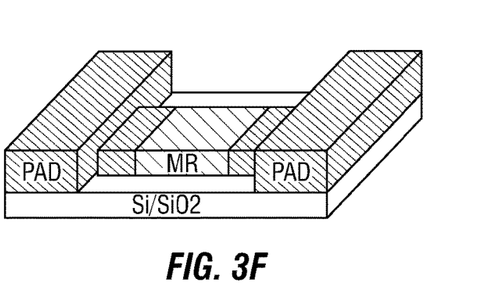

In some embodiments, a MR sensor system may be fabricated using various established semiconductor manufacturing processes. A nonlimiting schematic illustrating major fabrication steps is presented in FIGS. 3A-3F. In some embodiments, a MR film or sensor according to any of the embodiments discussed previously above may be deposited at a desired location, such as on a substrate. After deposition of the MR film, the MR film may be patterned into a desired pattern utilizing any suitable methods known. As a nonlimiting example, a bilayer resist may be deposited on top of the MR layer (FIG. 3A). Next, a first pattern may be formed by exposing the bilayer resist (FIG. 3B). In some embodiments, the pattern for the bilayer resist may provide a long line or T-shaped resist structure, where the lower layer of the bilayer resist may undercut the top layer of the bilayer resist. The undercut enables lift-off and improves contact between the leads and MR film (FIG. 3C). Next, the pattern is transferred into the MR film to remove portions of the MR film, such as via argon ion milling. After patterning the MR film, leads that are in contact with the MR film may be deposited on the substrate, and may incidentally be deposited on the T-shaped resist structure (FIG. 3C). Next, the T-shaped resist may be stripped off the MR and lead films. Next, the bilayer resist process discussed previously above may be repeated to produce another long line pattern or T-shaped resist structure on the MR film and lead (FIG. 3D). However, this second long line pattern or T-shaped resist structure is printed orthogonal to the first long line pattern/T-shaped resist structure. Next, the second pattern is transferred into the MR and lead films (FIG. 3E), such as via argon ion milling. Next, the resist may be stripped off the remaining MR and lead films. Next, pads may be deposited on the leads.

In a nonlimiting example of the fabrication discussed above, a MR film comprising (Ta 2.5 nm/Ru 5 nm/Co 5 nm/Ru 0.8 nm/Co 5 nm/Cu 6 nm/Co 5 nm/Ru 1.4 nm/Co 10 nm/Ta 5 nm) was deposited on oxidized Si wafers (500 nm SiO$_2$) via ultrahigh vacuum DC magnetron sputtering with a magnetic biasing holder. The MR film was then patterned into a 700 nm×600 nm rectangle using electron beam lithography. A nonlimiting example of the resist used in the lithography process is PMGI/PHOST bilayer. First, Microchem PMGI SF 4S was spin-coated to a thickness of 120 nm and baked at 170° C. for 2 minutes. Next, 15% PHOST dissolved in PGMEA was spin-coated to a thickness of 680 nm and baked at 170° C. for 2 minutes. As a nonlimiting example, a 700 nm wide and 200 µm long line pattern was exposed at a critical dose of 10,000 µC/cm$^2$; the PHOST was developed by immersing in PGMEA for 15 s. Next, the PMGI was undercut approximately 180 nm deep by immersing in MF-319 for 60 s. As a nonlimiting example, the pattern may be transferred to the MR film via argon ion milling. As a nonlimiting example, the leads may comprise Ta(2.5 nm)/Cu(50 nm)/Ta(10 nm) sputter deposited with the gun angles set at 45° with chuck rotation. As a nonlimiting example, the resist was stripped off by immersing in acetone with sonication. The previously discussed resist deposition and patterning processes may be repeated; however, this second T-shaped resist structure is printed orthogonal first T-shaped resist structure. The second pattern is transferred to the MR film and leads, and then the resist may be stripped off. As a nonlimiting example, the resist may be removed by immersion in acetone with sonication. The pad patterns were created using photolithography with an LOR/AZ1512 bilayer. As a nonlimiting example, the contact pads, Cr(10 nm)/Cu(100 nm), were deposited by sputtering. The sensor fabrication may be complete after a final lift-off in acetone with sonication.

It should be noted that fabrication steps discussed above are merely illustrative, a person of ordinary skill in the art shall recognize that various approaches may achieve the same structure using different instruments, processes and/or materials. For example, electron beam lithography can be substituted using photolithography or nanoimprinting. The bilayer resist comprising of PMGI/PHOST can be replaced with any suitable bilayer resist, such as, but not limited to, PMMA/HSQ. Further, the MR film may comprise any suitable materials and may be fabricated using any suitable process. The contact leads and contact pads may comprise of any variety of conductors known in the art. One important element of the fabrication is the T-shaped resist structure, which allows side contacts to the sensor.

Figure 4A:
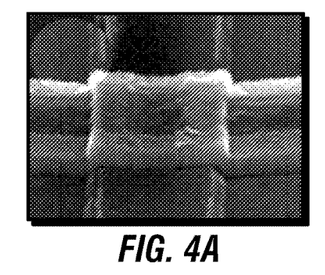
FIGS. 4A-4H demonstrate detection capabilities of two different quasi-digital MR sensors.
Figure 4B:
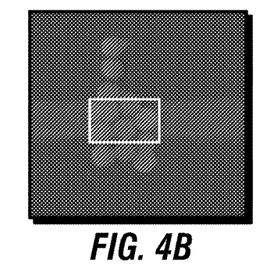
Figure 4C:
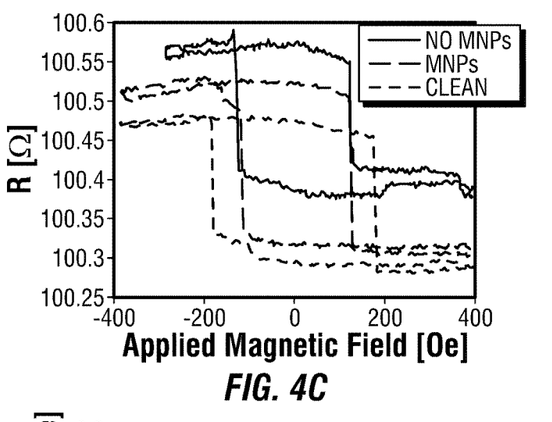
Figure 4D:
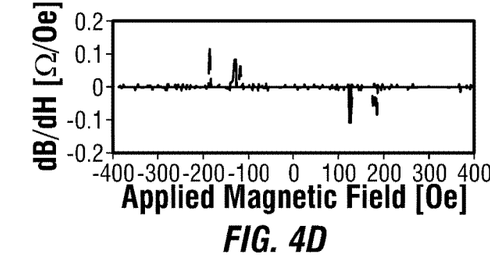
Figure 4E:
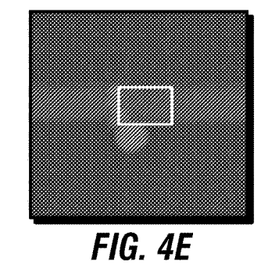
Figure 4F:
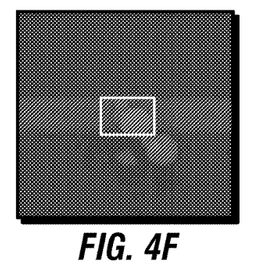
Figure 4G:
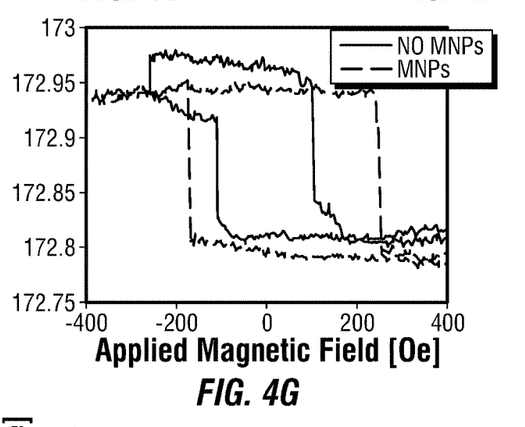
Figure 4H:
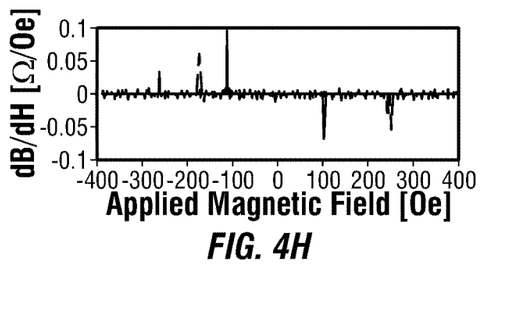

FIG. 4A-4H demonstrates the detection capabilities of two different quasi-digital MR sensors. The "large" MR sensor is approximately 6 times larger than a 500 nm Fe$_3$O$_4$ superparamagnetic MNP and the "small" MR sensor is approximately the same size as the 500 nm MNP. As utilized herein, small MR sensor(s) refer to sensors approximately the same size as a MNP utilized for detection, and large MR sensor(s) refer to sensors at least 2× larger than a MNP utilized for detection. FIGS. 4A-4B respectively show SEM images of the large MR sensor without and with a cluster of MNPs. Without any MNP on the large MR sensor, it switches between the low and high resistance states at approximately −125 Oe or +125 Oe (FIG. 4C). When there is a cluster of approximately 6 MNPs on the sensor, the switching field shifts outward to approximately −180 Oe or +180 Oe. Once the clusters of MNP on the sensor is cleaned off, the R-H curve returns to normal. The switching field can be determined by taking the derivative of the R-H curve (dR/dH) and locating the peak positions (FIG. 4D). Although the base resistance of the same sensor varies by nearly half of the total resistance change between the three measurements (No MNPs→MNPs→clean), the change in the switching field induced by the clusters of MNP is distinct and unambiguous.

Similarly, in FIGS. 4E-4H, a single particle shifts the switching field of the small MR sensor by approximately −50 or +150 Oe. The shift is asymmetric due to the position of the particle on the sensor. While the R-H loop of this particular small sensor is not ideal because there are multiple transitions caused by fabrication defects, such defects shall likely be corrected as fabrication processes improve.

Sensor Array

While small MR sensors using a quasi-digital detection scheme can detect a single MNP on the sensor surface using simple and low cost electronics, it is not very effective for biodiagnostic applications because it may be challenging to deliver the MNP to the surface of a single sensor surface. For example, if our sensor surface is 500×500 nm$^2$ and we can confine a dilute suspension of nanoparticles over a functionalized area of 100×100 um$^2$, the probability that a single MNP will land on the sensor and get detected is 0.0025%. Assuming that the landing event is completely random and does not depend on history, the probability of detecting at least one MNP can be estimated using the Poisson distribution:

$$P(k) = e^{-\lambda} \frac{\lambda^k}{k!}$$

where P(k) is the probability of k events per interval, λ is the average number of events per interval and k is a positive integer representing the number of events. The number of events per interval is:

$$\lambda = np$$

$$\lambda = n \frac{A_{sensor}}{A_{Surface}}$$

where n is the number of events and p is the probability of a successful event. The probability of a successful event is the ratio of the effective sensor area ($A_{sensor}$) to the functionalized area ($A_{surface}$). The sensor can detect nearby MNPs, so the effective sensor area is always larger than the actual sensor area. The functionalized area is a region on the chip where MNPs can specifically bind and is typically larger than the actual sensor area. When a particle lands on functional area without a sensor, it cannot be detected.

Figure 5:
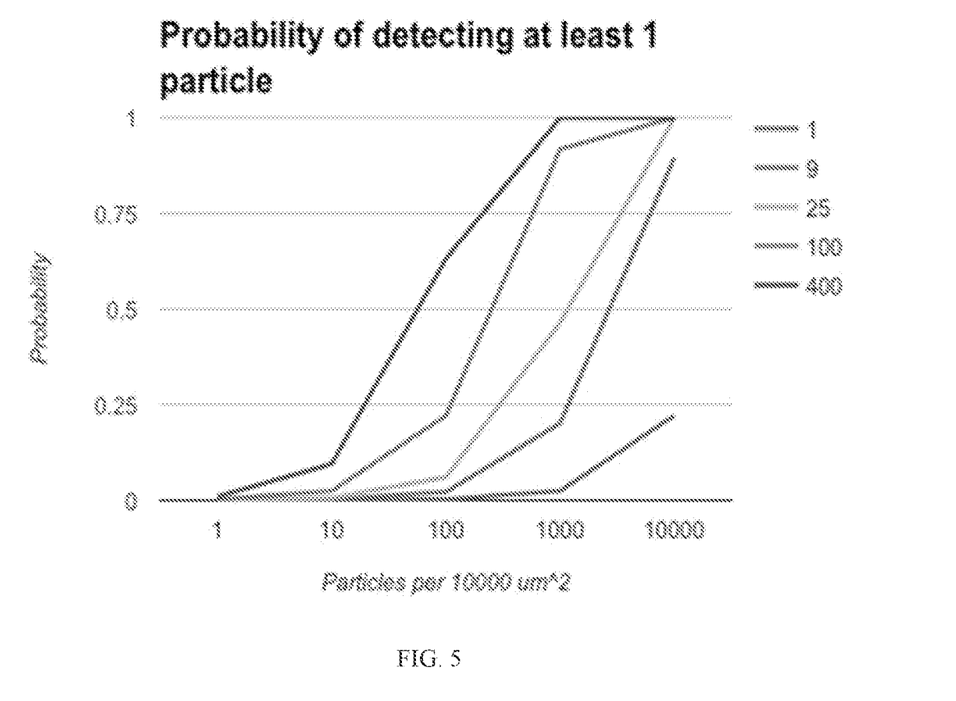
FIG. 5 is a graph showing the probability of detecting at least one MNP for arrays of sensors varying from 1 to 400.

FIG. 5 is a graph showing the probability of detecting at least one MNP for a single sensor, array of 9 sensors, array of 25 sensors, array of 100 sensors and an array of 400 sensors at a variety of MNP concentrations. Since A is proportional to n and p, the probability of detecting at least one particle increases monotonically with more particles and/or more sensors. Using 500×500 nm$^2$ sensors and a 100×100 um$^2$ functional area, by increasing the number of sensor from 1 to 400 and dropping 1000 particles within the functional area, the probability of detecting at least a single MNP increases from 0.2% to 100%.

Figure 6:
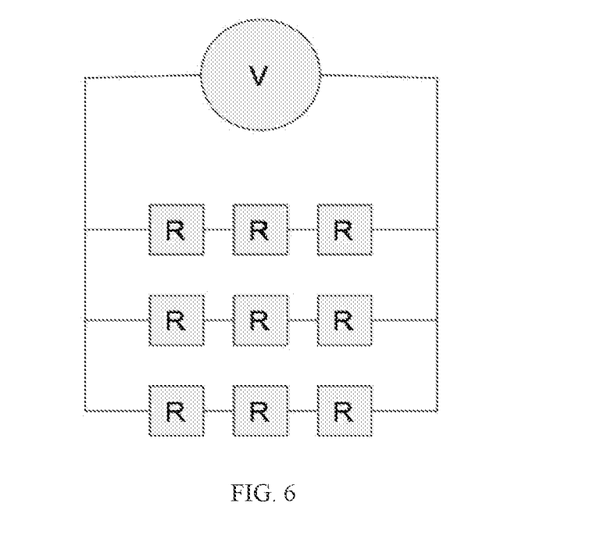
FIG. 6 is an illustrative embodiment of an array of sensors.

Increasing the number of sensors within the functional area effectively increases the probability that at least one MNP will randomly land on a sensor from the array of sensors. In some embodiments, any of the various embodiments of the MR sensor discussed above may be provided as part of an array of MR sensor. An array of sensors may be arranged where a set of N sensors are linked in series, as shown in FIG. 6. Further, N of these series linked sets are linked in parallel with a voltmeter or the like. The effective sensing area can be increased without degrading the detection speed; further, since all sensors are linked to a single voltmeter, the sensors are all probed simultaneously. In this configuration, the change in resistance due to a single sensor switching is:

$$\Delta R_T = \frac{\delta}{N^2 + N\delta - \delta}$$

where $\Delta R_T$ is the change in total resistance when a single particle is detected, N is the number of rows in the symmetric N×N array, and δ is the magnetoresistance ratio of the sensor. In addition to the symmetric N×N arrays, other embodiments of sensor arrays may be asymmetric $N_1 \times N_2$ arrays where $N_1 \neq N_2$. $N_1$ and $N_2$ are both integer values. The first value may indicate the number of sensors in series, and the second value may indicate the number of sensor sets in parallel, where each sensor set may comprise one or more sensors. For example, when 3 sensors are linked in series, it can be considered an array of 3×1. When 3 sensors are linked in parallel, it can be considered an array of 1×3. A 3×3 array describes 3 parallel lines with 3 sensors on each line, as shown in FIG. 6. A 5×3 array describes three parallel lines with 5 sensors on each line.

Figure 7A:
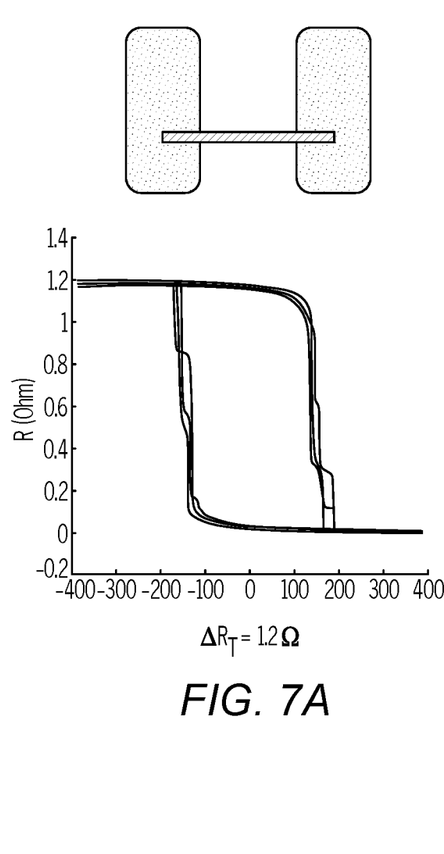
FIGS. 7A-7C showing the $\Delta R_T$-H loop of (a) 3 sensors in series, (b) a single sensor and (c) 3 sensors in parallel.
Figure 7B:
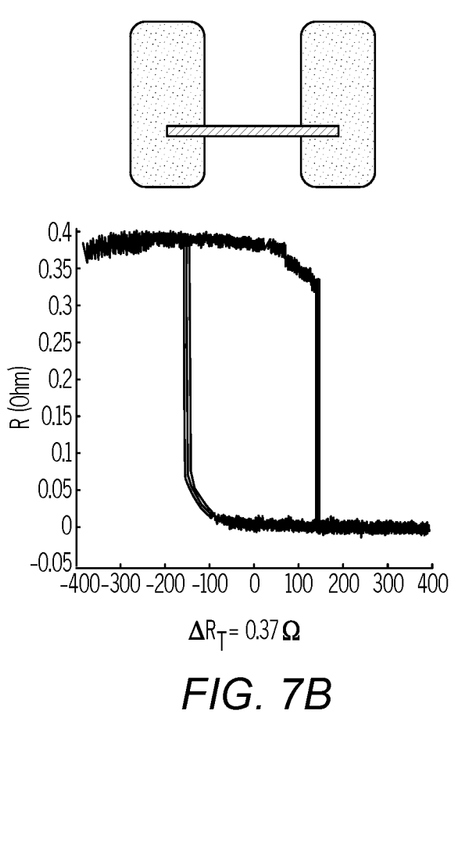
Figure 7C:
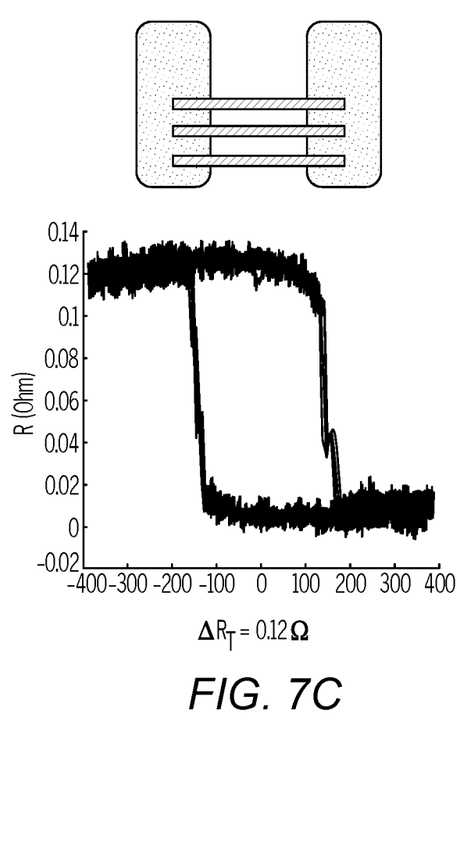

A preliminary proof of concept is shown in FIGS. 7A-7C showing the $\Delta R_T$-H loop of (a) 3 sensors in series, (b) a single sensor and (c) 3 sensors in parallel. In FIG. 7B, a single sensor switches digitally between the high and low resistance states. The change in resistance is 0.37Ω. When 3 sensors are linked in series (FIG. 7A), the total change in resistance is approximately 1.2Ω, which is the cumulative contribution of each sensor. Compared to a single transition for a single sensor, there are 3 distinct transitions for 3 sensors linked in series. The transition of individual sensors are visible in FIG. 7A because each sensor is slightly different due to fabrication imperfection. Similarly, 3 distinct transitions can be observed when 3 sensors are connected in parallel as shown in FIG. 7C. The total change in resistance is 0.12Ω because of the parallel configuration. These MR sensors behave just like resistors, their response when networked into an array can be predicted.

The detection of particles on an array of sensors is similar to a single sensor. For example, in a 3×3 array, the switching field transition is digitized into 9 segments. When a particle lands on any sensor in the array, the switching field of a single segment shall shift on the R-H curve. When a second particle lands on a different sensor, the switching field of another segment will shift. By counting the number of segments being shifted, it may be possible to determine the quantity of particles on the array.

Figure 8:
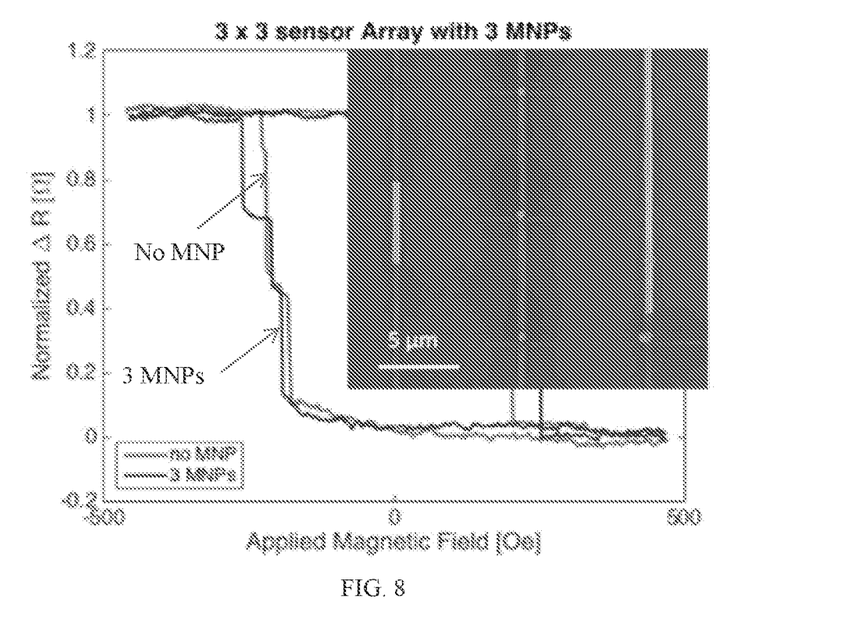
FIG. 8 shows normalized $\Delta R$ for a 3×3 sensor array with three MNPs.
Figure 9:
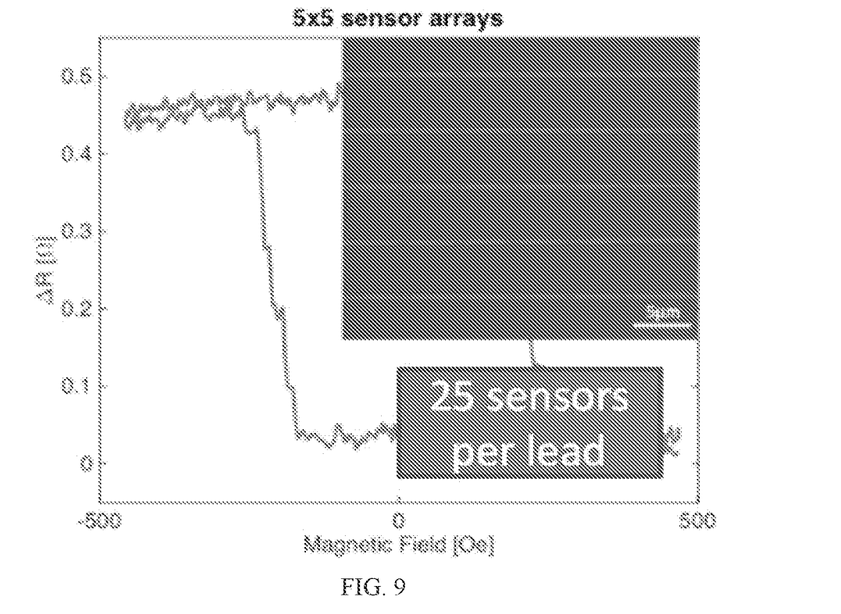
FIG. 9 shows $\Delta R$ for a 5×5 sensor array.

To demonstrate proof of concept for a sensor array, FIG. 8 shows sensor response for a 3×3 sensor array. The graph shows the sensor response with no particles and with 3 particles on 3 sensors. The inset is an SEM image of a 3×3 sensor array with 3 nanoparticles placed on the 3 sensors in the middle column. Significantly, approximately ⅓ of the sensors switch at a larger field when 3 out of 9 sensors have particles on them, as expected. FIG. 9 shows the response (RH-loop) of a 25 sensor array has a small distribution due to imperfections in fabrication and design.

Figure 10A:
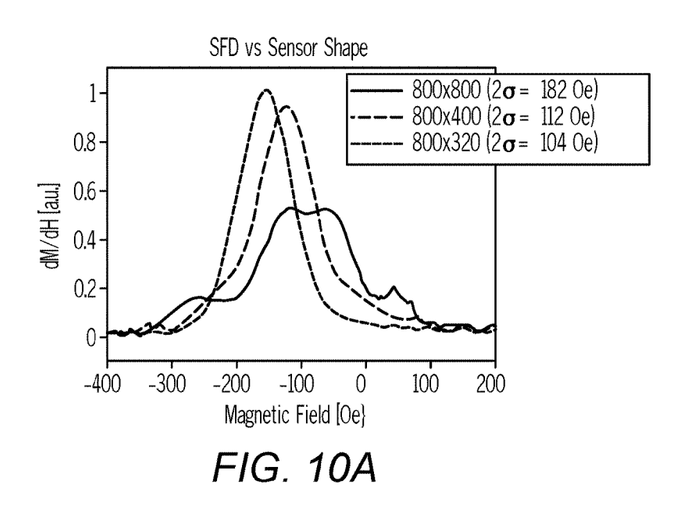
FIGS. 10A-10B respectively show switching field distribution (SFD) vs sensor shape and free layer material.
Figure 10B:
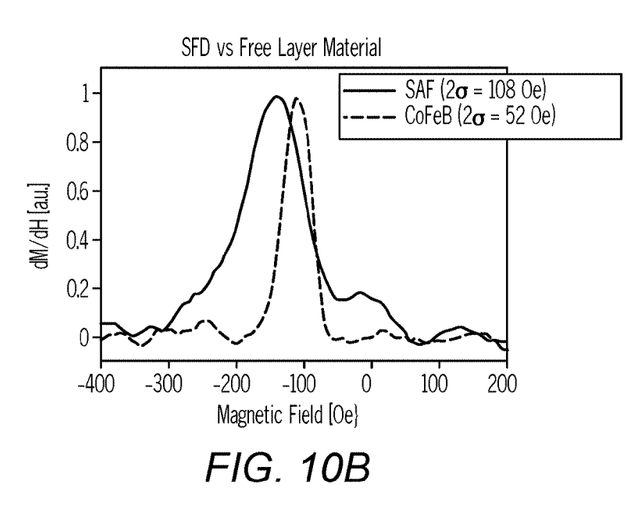

The switching field distribution can be improved by (a) changing the shape of the sensor from square to rectangular and (b) changing the free layer material from an asymmetric SAF to CoFeB. FIGS. 10A-10B respectively show SFD as a function of sensor shape and free layer material. These graphs are acquired by measuring chips with up to 25 million sensors each. A narrow switching field is important for biosensing application because it allows the difference between a switched state (nanoparticle is on a sensor) and non-switched state (no nanoparticles in proximity of the sensor) to be more easily identified.

Figure 11A:
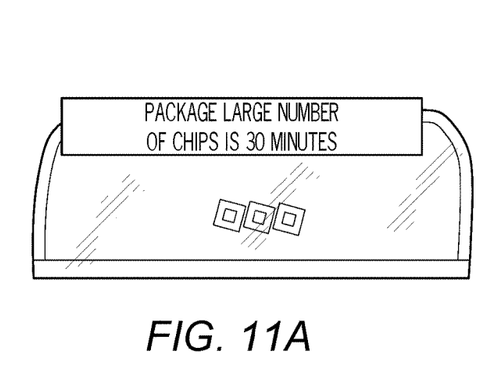
FIGS. 11A-11B respectively show vacuum sealing of multiple PCBs and a sensor chip and PCB suitable for connection to a reader.
Figure 11B:
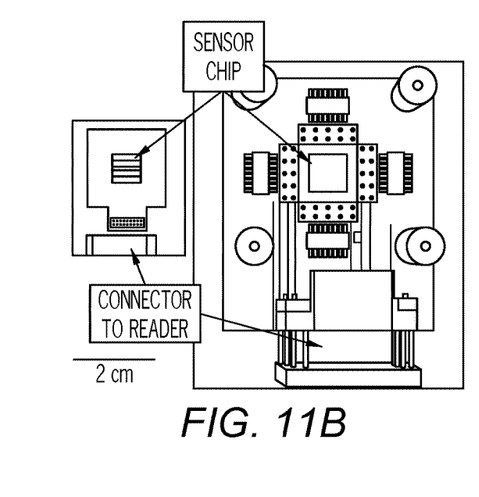

A low cost and high throughput approach to package the sensor into a fieldable device was also developed. In some embodiments, an anisotropic conducting film (ACF) is used to bond the sensor chip onto a printed circuit board (PCB). First, the PCB may be cleaned (e.g. IPA) and dried. An ACF may be applied to the sensor or PCB, and pressure and/or heat may be applied to bond the two together. As a nonlimiting example, the ACF may be a sheet of anisotropic conductive paste sandwiched between two plastic liners. The ACF may be cut to an appropriate size, such as with a laser cutter. One of the liners may be removed, and the ACF may be fixed to the contact pads on the PCB, such as by using finger pressure or the like and heating the ACF to 50° C. In some embodiments, the ACF may be screen printed onto the PCB. Multiple PCBs can be simultaneously fixed with ACF by using a vacuum sealer to apply uniform pressure as shown in FIG. 11A. The vacuum sealed PCBs may then be placed into a 50° C. oven for 10 minutes. Afterwards, each PCB is aligned to the sensor chip, such as by using a mask aligner. The ACF adhesive will temporarily bond them together when the chip is pressed against the PCB. Next, the ACF may be cured so that the chip and PCB units are permanently bonded. As a nonlimiting example, the chip and PCB units may be placed into a Nanoimprinter and processed at 100 psi and 200° C. for 5 minutes to cure the ACF and permanently bond the chip to the PCB. FIG. 11B shows a sensor chip and PCB suitable for connection to a reader.

The developed sensor technology discussed above represents a major advancement for magnetic biosensing. The new design is drastically different from prior state-of-the-art.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

What is claimed is:

1. A method for biochemical testing, the method comprising:
applying a first AC magnetic field sweep to a magnetoresistive (MR) sensor and measuring a resistance of the MR sensor for a change in a resistance state,
wherein a surface of the MR sensor is functionalized with a first analyte binding agent, wherein the MR sensor provides a quasi-digital response to a magnetic field sweep, and wherein the MR sensor comprises: a free layer that is ferromagnetic, a pinned layer that is ferromagnetic, and a nonmagnetic layer sandwiched between the free and the pinned layers, wherein when magnetization directions of the free and the pinned layers are parallel, the MR sensor is in a low-resistance state, and when the magnetization directions of the free and the pinned layers are perpendicular, the MR sensor is in a high-resistance state;
introducing an analyte to the MR sensor that is capable of interacting with the first analyte binding agent, wherein the introducing of the analyte occurs after applying the first AC magnetic field sweep to the MR sensor and measuring the resistance of the MR sensor for a change in the resistance state;
introducing magnetic nanoparticles (MNPs) functionalized with a second analyte binding agent capable of interacting with the analyte, wherein the introducing of the MNPs occurs after applying the first AC magnetic field sweep to the MR sensor and measuring the resistance of the MR sensor for a change in the resistance state; and
applying a second magnetic field sweep to the MR sensor again and measuring the resistance of the MR sensor for a change in the resistance state, wherein the applying of the second magnetic field sweep and measuring the resistance of the MR sensor for a change in the resistance state occur after introducing the MNPs and the analyte, and wherein a shift in a switching field where the sensor transitions between resistance states indicates a presence of at least one of the MNPs bound to the analyte on the MR sensor.

2. The method of claim 1, wherein the MR sensor is part of an array of MR sensors.

3. The method of claim 2, wherein the array of MR sensors are arranged in symmetric N×N array or the array of MR sensors are arranged in asymmetric $N_1 \times N_2$ array, where $N_1 \neq N_2$, $N_1$ represents a number of sensors in series, and $N_2$ represent a number of sensor sets in parallel.

4. The method of claim 1, wherein the free layer is an asymmetric synthetic antiferromagnet or a polycrystalline or amorphous ferromagnetic layer film, and the pinned layer is a symmetric synthetic antiferromagnet or a ferromagnetic layer with its magnetization pinned by adjacent antiferromagnetic layer.

5. The method of claim 1, further comprising a step of functionalizing the surface of the MR sensor with the first analyte binding agent.

6. The method of claim 1, wherein the first and second magnetic field sweeps are applied in a direction parallel to the MR sensor.

7. The method of claim 1, wherein the measurements of the resistance of the MR sensor for a change in the resistance state each occur during the application of the first and second AC magnetic field sweeps to the MR sensor.

* * * * *